United States Patent
O'Brien et al.

(10) Patent No.: US 10,037,875 B2
(45) Date of Patent: Jul. 31, 2018

(54) PROBE ASSEMBLY FOR ATTACHING A CHROMATOGRAPHY DEVICE TO A MASS SPECTROMETER

(71) Applicant: Micromass UK Limited, Wilmslow (GB)

(72) Inventors: Steve O'Brien, Manchester (GB); Ian Trivett, Cheadle (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

(21) Appl. No.: 15/023,528

(22) PCT Filed: Sep. 17, 2014

(86) PCT No.: PCT/GB2014/052816
§ 371 (c)(1),
(2) Date: Mar. 21, 2016

(87) PCT Pub. No.: WO2015/040384
PCT Pub. Date: Mar. 26, 2015

(65) Prior Publication Data
US 2016/0217992 A1     Jul. 28, 2016

(30) Foreign Application Priority Data

Sep. 23, 2013  (EP) .................................. 13185632
Sep. 23, 2013  (GB) .................................. 1316890.1

(51) Int. Cl.
*H01J 49/04* (2006.01)
*G01N 30/72* (2006.01)
(Continued)

(52) U.S. Cl.
CPC ........ *H01J 49/0404* (2013.01); *G01N 27/622* (2013.01); *G01N 30/7233* (2013.01);
(Continued)

(58) Field of Classification Search
CPC ............. G01N 27/622; G01N 30/7233; G01N 30/7266; G01N 30/7206; G01N 35/10;
(Continued)

(56) References Cited

U.S. PATENT DOCUMENTS

| 4,641,541 A | 2/1987 | Sharp |
| 5,175,433 A | 12/1992 | Browner et al. |

(Continued)

FOREIGN PATENT DOCUMENTS

JP     2009294086     12/2009

OTHER PUBLICATIONS

Herring et al., "*An On-Line Preconcentrator and the Evaluation of Electrospray Interfaces for the Capillary Electrophoresis/Mass Spectrometry of Peptides*", Rapid Communications in Mass Spectrometry, vol. 13, No. 1, pp. 1-7, 1999.
(Continued)

*Primary Examiner* — Wyatt Stoffa
(74) *Attorney, Agent, or Firm* — Deborah M. Vernon; Heath T. Misley; Womble Bond Dickinson (US) LLP

(57) ABSTRACT

A probe assembly is disclosed comprising an inlet for receiving an eluent from a chromatography device; an outlet for delivering the eluent to an ion source of a mass spectrometer; and an attachment device for attaching the outlet to the mass spectrometer. The outlet comprises an electrically conductive capillary and an electrically conductive member surrounding at least part of the electrically conductive capillary. The electrically conductive member is arranged to receive a voltage upon connection of the attachment device to the mass spectrometer and the electrically conductive member is arranged to provide an electrical connection from the electrically conductive member to the electrically conductive capillary.

16 Claims, 5 Drawing Sheets

(51) Int. Cl.
*H01J 43/24* (2006.01)
*H01J 47/00* (2006.01)
*G01N 27/62* (2006.01)

(52) U.S. Cl.
CPC .......... *G01N 30/7266* (2013.01); *H01J 43/24* (2013.01); *H01J 47/005* (2013.01); *H01J 49/0431* (2013.01)

(58) Field of Classification Search
CPC .. H01J 49/0404; H01J 49/0431; H01J 49/165; H01J 49/04; H01J 49/0422; H01J 49/167
See application file for complete search history.

(56) References Cited

U.S. PATENT DOCUMENTS

| | | | |
|---|---|---|---|
| 6,043,487 A * | 3/2000 | Waki | H01J 49/167 250/281 |
| 6,753,521 B1 | 6/2004 | Park et al. | |
| 7,075,066 B2 * | 7/2006 | Bailey | H01J 49/165 250/281 |
| 7,960,711 B1 | 6/2011 | Sheehan et al. | |
| 8,227,750 B1 | 7/2012 | Zhu et al. | |
| 8,384,026 B2 | 2/2013 | O'Malley et al. | |
| 8,723,109 B2 | 5/2014 | Newton | |
| 8,759,758 B2 | 6/2014 | Steiner et al. | |
| 9,188,569 B2 | 11/2015 | Graham | |
| 9,459,240 B2 | 10/2016 | Vorm | |
| 2005/0023455 A1 * | 2/2005 | Bailey | H01J 49/165 250/288 |
| 2005/0061673 A1 * | 3/2005 | Presto Elgstoen | G01N 27/44717 204/601 |
| 2014/0305801 A1 | 10/2014 | Peterson et al. | |
| 2016/0217992 A1 | 7/2016 | O'Brien et al. | |

OTHER PUBLICATIONS

Jackson et al., "*Electrical Equivalence of Electrospray Ionization with Conducting and Nonconducting Needles*", Analytical Chemistry, vol. 71, No. 17, pp. 3777-3784, 1999.

Kertesz et al., "*Minimizing Analyte Electrolysis in an Electrospray Emitter*", Journal of Mass Spectrometry, vol. 36, No. 2, pp. 204-210, 2001.

* cited by examiner

PROBE ASSEMBLY FOR ATTACHING A CHROMATOGRAPHY DEVICE TO A MASS SPECTROMETER

CROSS REFERENCE TO RELATED APPLICATIONS

This application is the National Stage of International Application No. PCT/GB2014/052816, filed 17 Sep. 2014 which claims priority from and the benefit of United Kingdom patent application No. 1316890.1 filed on 23 Sep. 2013 and European patent application No. 13185632.1 filed on 23 Sep. 2013. The entire contents of these applications are incorporated herein by reference.

BACKGROUND OF THE PRESENT INVENTION

This invention relates generally to probe assemblies for mass spectrometers. The preferred embodiment of this invention relates to atmospheric pressure ionisation probes for use with mass spectrometry systems.

Liquid chromatography systems are an important tool to the analytical chemist for the separation and analysis of samples of interest. Often, after separation in the liquid chromatograph, the components require further analysis to confirm the identity of these components. This is generally best performed using a mass spectrometer. However, connecting liquid chromatography systems to mass spectrometers can be a difficult and time consuming task. For example, in recent years the volume of eluent produced from liquid chromatography systems at any given time has reduced, leading to the provision of smaller, more delicate tubing and smaller connecting assemblies for connecting the tubing to other instruments.

The tubing may need to deliver eluent to an electrospray ion source, wherein the eluent from the liquid chromatography system is sprayed into the ion source chamber through a capillary which has an electrical voltage applied to it. This results in an awkward connection that requires dexterity and skill to assemble. Moreover, there is a risk of electric shock at the connection for the user assembling the instrument connection if there is a leak. The connecting assembly can also be expensive.

Furthermore, the fitting of the liquid chromatography tube connection into an Electrospray source can take a long time, resulting in inactivity of the instrument. Poor instrument performance may also occur if parts are omitted or poorly assembled. This can result in dead volumes, which may lead to poor reproducibility or poor performance of the instrument.

It is therefore desirable to provide an improved probe assembly. For example, embodiments of the present invention provide a probe assembly which is cheap, easy to fit and is adapted to remove any risk of electric shock to the user fitting the device.

SUMMARY OF THE PRESENT INVENTION

From a first aspect the present invention provides a probe assembly comprising:
an inlet for receiving an eluent from a chromatography device;
an outlet for delivering the eluent to an ion source of a mass spectrometer; and
an attachment device for attaching the outlet to the mass spectrometer;
wherein the outlet comprises an electrically conductive capillary and an electrically conductive member surrounding at least part of the electrically conductive capillary;
wherein the probe assembly comprises an insulating fluid line for transporting eluent from the inlet to the electrically conductive capillary and a joint between the insulating fluid line and the electrically conductive capillary, wherein the joint is downstream of the attachment device; and
wherein the electrically conductive member is arranged to receive a voltage upon connection of the attachment device to the mass spectrometer and the electrically conductive member is arranged to be in electrical connection with the electrically conductive capillary.

The present invention provides a probe assembly for delivering eluent to a mass spectrometer, wherein the joint between the electrically insulated fluid line and the conductive capillary is downstream of the attachment device that attaches the probe to the spectrometer. As such, the eluent is less likely to leak out of the spectrometer when the probe is attached, which is problematic for a number of reasons, including a risk of electrocution to the user. A conductive member is provided in order to supply a voltage from the attachment device, downstream beyond the insulated fluid line and to the conductive capillary. This enables a voltage to be supplied relatively easily from the mass spectrometer to the conductive capillary via the attachment device, even though the electrically insulated fluid line is interposed between the attachment device and the conductive capillary. The structure of the probe therefore enables the electrical connection to be made between the spectrometer and the conductive capillary relatively quickly and easily.

WO 03/042684 discloses an interface between a capillary electrophoresis device and a mass spectrometer. Referring to FIG. 3 of this document, the device is connected to the mass spectrometer by a screw 21. The device comprises a capillary 5 that runs through an electrolyte hose 7. The hose 7 is secured into the screw 21 by fixing screw 20. The hose 7 terminates in the screw housing 21 and the capillary continues through an electrode 10. The electrode 10 is secured into the screw 21 by a screw 25 such that a junction is formed between the hose 7 and the electrode 10 within the screw 21. As such electrolyte is able to flow from the hose 7 into the annular region between the capillary 5 and the surrounding electrode 10.

However, WO 03/042684 does not provide the joint between the hose and the capillary electrode downstream of the screw that attaches the device to the mass spectrometer. In contrast, it is essential in WO 03/042684 that the joint is provided within the screw that attaches the device to the mass spectrometer, because the hose and the electrode are screwed into opposite ends of the screw that attaches the device to the mass spectrometer. As the joint is not downstream of the screw that attaches the device to the spectrometer, the arrangement is less able to prevent leakage of fluids out of the spectrometer, as compared to the present invention.

Preferably, the outlet of the probe assembly is configured to be insertable into an orifice of the mass spectrometer and the attachment device is configured so as to releasably engage the orifice so as to releasably attach the probe to the mass spectrometer.

The joint is arranged in the probe so as to be downstream of the orifice (i.e. within the spectrometer) when the attachment device is connected to the spectrometer.

It will be appreciated that the term "downstream" used herein refers to the direction from the inlet end to the outlet end of the probe assembly.

Preferably, the attachment device comprises a screw fitting, a clamp, or a bayonet.

The screw fitting preferably comprises threads that extend circumferentially around the insulating fluid line for engaging an orifice in the spectrometer into which the probe is inserted, in use. The screw fitting and threads are preferably on an outer surface of the attachment device. Alternatively, the releasable engagement may be provided by other attachment means, or any form of attachment means which does not require tools to fit.

Preferably, the attachment device comprises a first electrical contact for receiving said voltage from the spectrometer when the attachment device is releasably connected thereto, wherein the electrical contact is connected to the conductive member and the conductive member is connected to the conductive capillary for transmitting the voltage from the spectrometer to said conductive capillary. Preferably, said electrical contact is on an outer surface of the attachment device.

Optionally, the electrical contact is a ferrule.

The electrical contact (e.g. ferrule) may be an integral or non-integral part of the attachment device. However, the electrical contact forms part of the attachment device such that when the attachment device is releasably connected to the spectrometer, the electrical contact is connected to the spectrometer and the conductive member for transmitting said voltage from the spectrometer to said conductive capillary. The electrically conductive member preferably surrounds said joint. The electrically conductive member is able to transmit said voltage from the attachment device, downstream of the electrically insulating fluid line and to the conductive capillary.

Preferably, the electrically conductive member is an electrically conductive tube. The tube preferably extends from being in contact with the electrical contact on the attachment device to being in contact with the conductive capillary.

The electrical connection from the electrically conductive member to the electrically conductive capillary may be performed by tabs in the electrically conductive member; and/or the electrical connection from the electrically conductive member to the electrically conductive capillary may be performed by an electrically conductive packing between the electrically conductive member and the electrically conductive capillary.

The electrically conductive member is preferably arranged to receive said voltage upon connection of the attachment device to the mass spectrometer through an electrically conductive ferrule.

Optionally, the conductive capillary is configured to spray eluent from its outlet.

Optionally, the conductive capillary is configured so as to transmit said voltage to the eluent being sprayed therefrom for forming charged droplets of eluent.

Preferably, the electrically conductive capillary is an electrospray capillary.

Preferably, the inlet for receiving the eluent is spaced from the attachment device.

The probe has an inlet attachment device disposed towards one end of the probe and an outlet attachment device disposed towards the other end of the probe.

The probe assembly preferably further comprises an inlet attachment device for attaching the inlet to a chromatography device.

Optionally, the inlet of the probe is configured to be insertable into an orifice of the chromatography device and the inlet attachment device is configured so as to releasably engage the orifice so as to releasably attach the probe to the chromatography device.

Preferably, the inlet attachment device comprises a screw fitting, a clamp or a bayonet. The screw fitting preferably comprises threads that extend circumferentially about the insulating fluid line for engaging an orifice in the chromatography device. The screw fitting and threads are preferably on an outer surface of the inlet attachment device. Alternatively, the releasable engagement may be provided by other attachment means, or any form of attachment means which does not require tools to fit.

The present invention also provides a mass spectrometer or ion mobility spectrometer adapted to be connectable with a probe assembly as described herein.

The present invention also provides a system comprising a spectrometer as described herein and the probe assembly described herein, wherein the outlet attachment device of the probe assembly and the spectrometer housing are configured such that the outlet attachment device is releasably engagable with an orifice in the spectrometer housing so as to connect the probe assembly to the mass spectrometer with the probe assembly outlet inserted into the orifice.

Preferably, the mass spectrometer of the system comprises a voltage supply and a second electrical contact located proximate to the orifice for supplying said voltage to the conductive capillary of the probe assembly. The second electrical contact is preferably arranged and configured such that when the outlet attachment device of the probe assembly is engaged with the orifice, the second electrical contact engages with said first electrical contact on the outlet attachment device for supplying the voltage from the voltage supply to the conductive capillary.

Optionally, the spectrometer comprises means for preventing the voltage from being applied to the probe assembly until the probe outlet attachment device is fully connected with the spectrometer. The means may comprise a sensor for detecting when the outlet attachment device is fully connected to the spectrometer.

Optionally, the spectrometer comprises a nebuliser tube and a gas supply for supplying gas through the nebuliser tube, and the probe outlet may be configured to be inserted through said orifice into the nebuliser tube.

Optionally, the system further comprises a chromatography device, wherein the probe assembly has a probe inlet configured to be releasably attached to the chromatography device so as to receive eluent from the chromatography device.

From a second aspect, the present invention provides a probe assembly for receiving eluent and delivering it through an orifice in a housing of a mass spectrometer or ion mobility spectrometer, said probe assembly comprising:

an electrically insulated fluid line having a fluid inlet for receiving eluent;

an electrically conductive capillary joined to said fluid line for receiving said eluent and having a fluid outlet for delivering the eluent into said spectrometer;

an attachment member surrounding said insulated fluid line, wherein the join between the insulated fluid line and the conductive capillary is located downstream of the attachment member, and wherein the attachment member is configured to releasably engage the spectrometer when the capillary and part of the fluid line are inserted through said orifice;

a first electrical contact on said attachment member for engaging an electrical contact on said spectrometer when the capillary and fluid line are inserted through said orifice and the attachment member is releasably engaged with the spectrometer; and a conductive member extending downstream from said electrical contact, passed said join between the insulated fluid line and the capillary, and into contact with said capillary for supplying a voltage from said first electrical contact to said capillary.

The join is arranged in the probe so as to be downstream of the orifice when the attachment member is connected to the spectrometer.

Preferably, the attachment member comprises a screw fitting, a clamp, or a bayonet for releasably engaging the spectrometer when the capillary and fluid line are inserted through said orifice.

The screw fitting preferably comprises threads that extend circumferentially around the insulating fluid line for engaging an orifice in the spectrometer into which the probe is inserted, in use. The screw fitting and threads are preferably on an outer surface of the attachment member.

Alternatively, the releasable engagement may be provided by other releasable attachment means, or any form of attachment means which does not require tools to fit.

Preferably, said first electrical contact is on an outer surface of the attachment member. The first electrical contact may be a ferrule.

The electrical contact (e.g. ferrule) may be an integral or non-integral part of the attachment member. However, the electrical contact forms part of the attachment member such that when the attachment member releasably engages the spectrometer, the electrical contact is connected to the spectrometer and the conductive member for transmitting said voltage from the spectrometer to said conductive capillary.

Preferably, the electrically conductive member is an electrically conductive tube that extends from the first electrical contact on the attachment member to the capillary.

Optionally, the electrical connection from the electrically conductive member to the electrically conductive capillary is performed by tabs in the electrically conductive member, and/or by an electrically conductive packing between the electrically conductive member and the electrically conductive capillary.

Preferably, the conductive capillary is configured to spray eluent from its outlet.

Preferably, the conductive capillary is configured so as to transmit said voltage to the eluent being sprayed therefrom for forming charged droplets of eluent.

The electrically conductive capillary is preferably an electrospray capillary.

Preferably, the inlet for receiving the eluent is spaced from the attachment member.

Preferably, said attachment member is disposed towards an outlet end of the probe assembly and the probe assembly has another attachment member disposed towards an inlet end of the probe assembly for attaching the inlet to a chromatography device or other source of analyte solution.

Optionally, the inlet of the probe is configured to be insertable into an orifice of the chromatography device or other source of analyte solution and the inlet attachment member is configured so as to releasably engage the orifice so as to releasably attach the probe assembly to the chromatography device or other source of analyte solution.

Preferably, the inlet attachment member comprises a screw fitting, a clamp or a bayonet. The screw fitting preferably comprises threads that extend circumferentially about the insulating fluid line for engaging an orifice in the chromatography device or other source of analyte solution. The screw fitting and threads are preferably on an outer surface of the inlet attachment member.

Alternatively, the releasable engagement may be provided by other attachment means, or any form of attachment means which does not require tools to fit.

The present invention also provides a system comprising a mass spectrometer or ion mobility spectrometer and the probe assembly described herein, wherein the spectrometer comprises a housing having an orifice therein for receiving said probe assembly therethrough, wherein the attachment member of the probe and the spectrometer housing are configured such that the attachment member is releasably engagable with the orifice so as to connect the probe assembly to the spectrometer with the capillary and part of the insulated fluid line inserted through the orifice, wherein the spectrometer comprises a voltage supply and a second electrical contact, and wherein the second electrical is arranged in the spectrometer so as to engage the first electrical contact on the probe assembly when the probe assembly has been releasably engaged with the orifice.

The system has a number of optional features. For example, the orifice may be located in an ion source of the spectrometer such that the capillary of the probe assembly extends into the ion source when the probe assembly is releasably engaged with the spectrometer.

The attachment member preferably has engaging elements that releasably engage with complementary engagement elements on the spectrometer housing for enabling said releasable engagement of said probe assembly to said spectrometer.

Preferably, the engaging elements on the attachment member are screw threads and the engaging elements on the spectrometer are complementary screw threads.

A seal may be provided on the attachment member and/or in the spectrometer proximate the orifice for providing a fluid seal between the probe assembly and the spectrometer when the probe assembly is releasably engaged with the spectrometer.

Optionally, the spectrometer comprises means for preventing the voltage from being applied to the probe assembly until the probe outlet attachment member is fully connected with the spectrometer. The means may comprise a sensor for detecting when the outlet attachment member is fully connected to the spectrometer.

Optionally, the spectrometer comprises a nebuliser tube and a gas supply for supplying gas through the nebuliser tube, and the probe outlet may be configured to be inserted through said orifice into the nebuliser tube.

The system preferably comprises a chromatography device or other source of analyte solution or eluent, wherein the probe assembly has a probe inlet configured to be attached to the chromatography device or other source so as to receive the solution or eluent.

Optionally, the inlet of the probe is configured to be insertable into an orifice of the chromatography device or other source of analyte solution and the probe assembly has an inlet attachment member configured so as to releasably engage the orifice so as to releasably attach the probe assembly to the chromatography device or other source of analyte solution.

The inlet attachment member preferably has engaging elements that releasably engage with complementary engagement elements on the chromatography device or other source of analyte solution for enabling said releasable engagement of said probe assembly to said chromatography device or other source of analyte solution. The engaging elements on the attachment member are preferably screw threads and the engaging elements on the chromatography device or other source of analyte solution are preferably complementary screw threads.

The inlet attachment member may comprise a screw fitting, a clamp or a bayonet. The screw fitting preferably comprises threads that extend circumferentially about the insulated fluid line for engaging an orifice in the chromatography device or other source of analyte solution. The screw fitting and threads are preferably on an outer surface of the inlet attachment member.

Alternatively, the releasable engagement may be provided by other attachment means, or any form of attachment means which does not require tools to fit.

The present invention also provides a method of delivering eluent to a mass spectrometer or ion mobility spectrometer comprising:

providing a system as described herein;

inserting the outlet end of the probe assembly into said orifice;

releasably engaging the attachment member of the probe assembly with the spectrometer such that the first electrical contact of the probe assembly engages the second electrical contact of the mass spectrometer;

supplying said voltage to said second electrical contact such that the voltage is applied to the conductive capillary; and supplying eluent into the insulated fluid line such that the eluent is transmitted through the conductive capillary and into the spectrometer.

The method preferably comprises ionising the eluent or analyte solution in the spectrometer.

The mass spectrometer may comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may comprise an electrostatic ion trap or mass analyser that employs inductive detection and time domain signal processing that converts time domain signals to mass to charge ratio domain signals or spectra. Said signal processing may include, but is not limited to, Fourier Transform, probabilistic analysis, filter diagonalisation, forward fitting or least squares fitting.

The mass spectrometer may comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The mass spectrometer may comprise a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The mass spectrometer may comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide is preferably maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

Analyte ions may be subjected to Electron Transfer Dissociation ("ETD") fragmentation in an Electron Transfer Dissociation fragmentation device. Analyte ions are preferably caused to interact with ETD reagent ions within an ion guide or fragmentation device.

Optionally, in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions preferably comprise peptides, polypeptides, proteins or biomolecules.

Optionally, in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

The process of Electron Transfer Dissociation fragmentation may comprise interacting analyte ions with reagent ions, wherein the reagent ions comprise dicyanobenzene, 4-nitrotoluene or azulene reagent ions.

According to one aspect, the present invention provides a probe assembly comprising:

an inlet for receiving an eluent from a chromatography device;

an outlet for delivering the eluent to an ion source of a mass spectrometer; and an attachment device for attaching the outlet to the mass spectrometer;

the outlet comprising an electrically conductive capillary and an electrically conductive member surrounding at least part of the electrically conductive capillary;

wherein the electrically conductive member is arranged to receive a voltage upon connection of the attachment device to the mass spectrometer and the electrically conductive member is arranged to be in electrical connection with the electrically conductive capillary.

Preferably, the probe assembly may further comprise an insulating fluid line for transporting eluent from the inlet to the electrically conductive capillary.

In the preferred embodiment the probe assembly may further comprise a joint between the insulating fluid line and the electrically conductive capillary.

In some embodiments the joint between the insulating fluid line and the electrically conductive capillary may be downstream of the attachment device.

In the preferred embodiment the attachment device may comprise a screw fitting.

In some embodiments the probe assembly further comprises an inlet attachment device for attaching the inlet to the chromatography device.

Preferably the inlet attachment device may comprise a screw fitting.

In the preferred embodiment the electrical connection from the electrically conductive tube to the electrically conductive capillary may be performed by tabs in the electrically conductive tube.

In some embodiments the electrical connection from the electrically conductive tube to the electrically conductive capillary may be performed by an electrically conductive packing between the electrically conductive tube and the electrically conductive capillary.

In the preferred embodiment the electrically conductive member may be arranged to receive a voltage upon connection of the attachment device to the mass spectrometer through an electrically conductive ferrule.

In another aspect of the invention there may be provided a mass spectrometer adapted to connect to a probe assembly as described above.

In a further aspect of the invention there may be provided a chromatography device and mass spectrometer adapted to connect to a probe assembly as described above.

It may be advantageous that the probe can be made in a range of inlet bore sizes and lengths to suit the required application The probe assembly may be arranged so that there would be no separate high voltage connection cables are required to be attached to the probe. It would therefore result in the user not requiring to connect or disconnect any cables.

In the preferred embodiment the present invention provides the easy attachment and removal of the probe assembly from the mass spectrometer.

The probe assembly of the present invention also reduces the danger of any electrical shock to be suffered by the user in the attachment and removal of the probe from the mass spectrometer. This is partly due to no fluid being capable of leaking within the probe assembly, or alternatively because no electrical connections external to the housing of the mass spectrometer are present. Additionally, the mass spectrometer may be adapted to only allow high voltage to be applied to the connections when the probe has been fully inserted into the instrument. This can be performed by software or hardware, either by preventing high voltage to be applied when the outer housing is closed, or by sensors preventing the voltage from being applied when the probe is not tightly screwed into the mounting of the mass spectrometer.

It would be apparent to the skilled person that the probe of the present invention would be of lower cost than prior art probe assemblies.

In the preferred embodiment an integral electrical connection from the outer electrically conductive tube to the capillary ensures efficient voltage transfer to the conductive capillary once the device is fully inserted, and high voltage is turned on.

Prior art probe assemblies often require connection to the top of the ion source enclosure of mass spectrometers. In some cases, the probe assemblies are often mechanically fixed and require to be removed when the capillary requires changing. Additionally, often electrical supply cables require disconnecting. This process is often of considerable difficulty for users and requires correct assembly to ensure correct operation. In some prior art assemblies, a user may receive an electrical shock in the event that fluid is present upon attempting to remove the probe assembly. Some prior art assemblies also enable sample fluid to leak from the instrument. This is not only undesirable in that it results in a loss of sample, but the fluid may pose a hazard to the user or instrument itself. Such leakage may also corrupt the experiment being performed.

Due to the design of the probe assembly according to the present invention, the user is protected from electrical shock from the capillary when touching the probe connection, because the electrical connection between the probe and the mass spectrometer housing can only be made when the probe is attached to the mass spectrometer by the outlet attachment device. Furthermore, the probe assembly further protects electric shocks and the other disadvantages discussed above, by the removal of the danger of leaks within the probe assembly.

The probe assembly of the present invention may be changed in seconds with no tools.

The probe assembly of the present invention features fixed positions within the assembly to provide consistent and reliable positioning of the probe within the mass spectrometer. For example, the predetermined distance between the attachment device and the distal end of the conductive capillary controls the distance that the conductive capillary protrudes into the spectrometer in use. This may result in more reproducible results from the mass spectrometer and may reduce the level of skill required from the user to fit the assembly.

The features of the probe assembly of the present invention are specifically designed to enable the quick removal and attachment of the probe assembly. This is desirable because this reduces the down time of the instrument. The present probe assembly typically can be removed, or replaced within about 30 seconds. Previous probe assemblies typically could take up to 30 minutes to replace.

These features may be particularly suited to be designed for miniature or smaller mass spectrometers. Smaller space required on the source enclosure meaning the probe assembly fits well to smaller mass spectrometry machines. Additionally, the present probe assembly is easier to insert, requiring less insertion clearance than previous probes. This may be particularly useful for a mass spectrometer inserted into a Liquid chromatography stack. The more limited clearance available may be as a result of protruding connections, and other objects in other devices in the Liquid chromatography stack above or below the mass spectrometer.

Prior art probe assemblies require the user to connect the capillary into the probe assembly. Should the connection of the capillary, or the assembly not be made correctly or tightly enough the connection between the mass spectrometer and the probe assembly may leak fluid, gas or both. It would be apparent to the skilled person that this presents a safety hazard, and the performance of the instrument may be impaired.

The probe assembly according to the present invention is designed to prevent fluid or gas leaks from escaping outside the source enclosure. This prevents the danger of any harmful solvents or samples escaping from the probe assembly. In some embodiments any fluid or gas leaks can be detected by sensors within the instrument.

The present invention presents a single assembly which is cheap to produce, and may be a disposable unit.

In prior art probes, leaks may be detected by detection systems within the mass spectrometer housing should they occur. In the present invention, the need for leak detectors may be removed by the removal of the main cause of leaks—the poor assembly of the probe structure by the user.

BRIEF DESCRIPTION OF THE DRAWINGS

Various embodiments of the present invention will now be described, by way of example only, and with reference to the accompanying drawings in which.

DETAILED DESCRIPTION OF PREFERRED EMBODIMENTS

Figure 1:
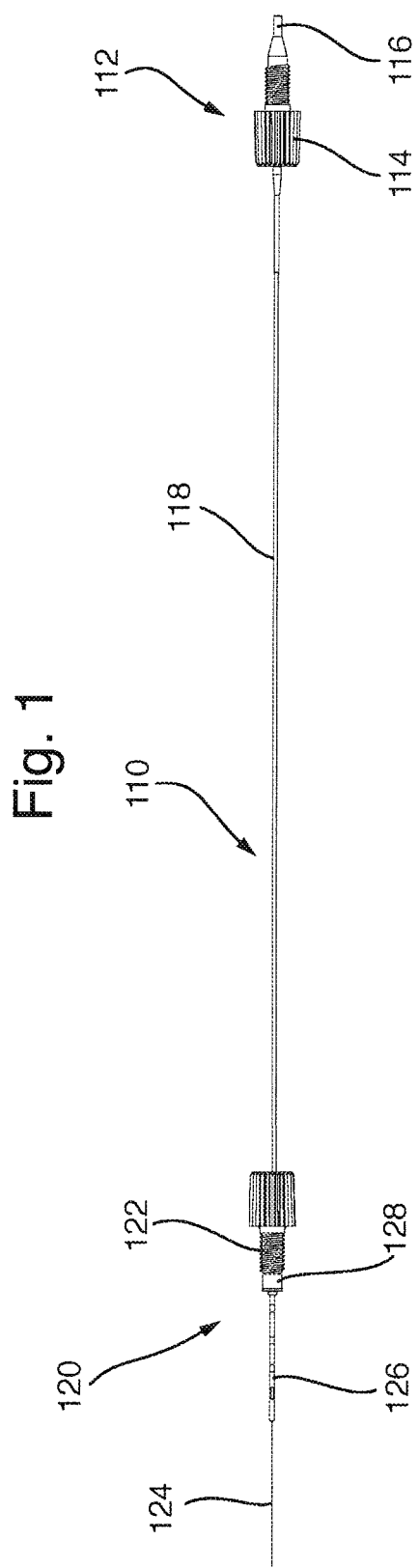
FIG. 1 is an illustration of a probe assembly according to a preferred embodiment of the present invention.

FIG. 1 shows a probe assembly 110 according to an embodiment of the present invention. The probe assembly 110 has an inlet end 112 having an inlet attachment fitting 114 that is configured for attaching the probe to a liquid chromatography device (not shown). A fluid inlet 116 is located at the inlet end 112 of the probe and is arranged to be insertable into a liquid chromatography output (not shown) such that the fluid inlet 116 receives eluent from the liquid chromatography instrument. An electrically insulating fluid line 118 runs from the fluid inlet 116 to an outlet end 120 of the probe. The inlet end 112 of the probe will be described in more detail in relation to FIG. 4.

Figure 2:
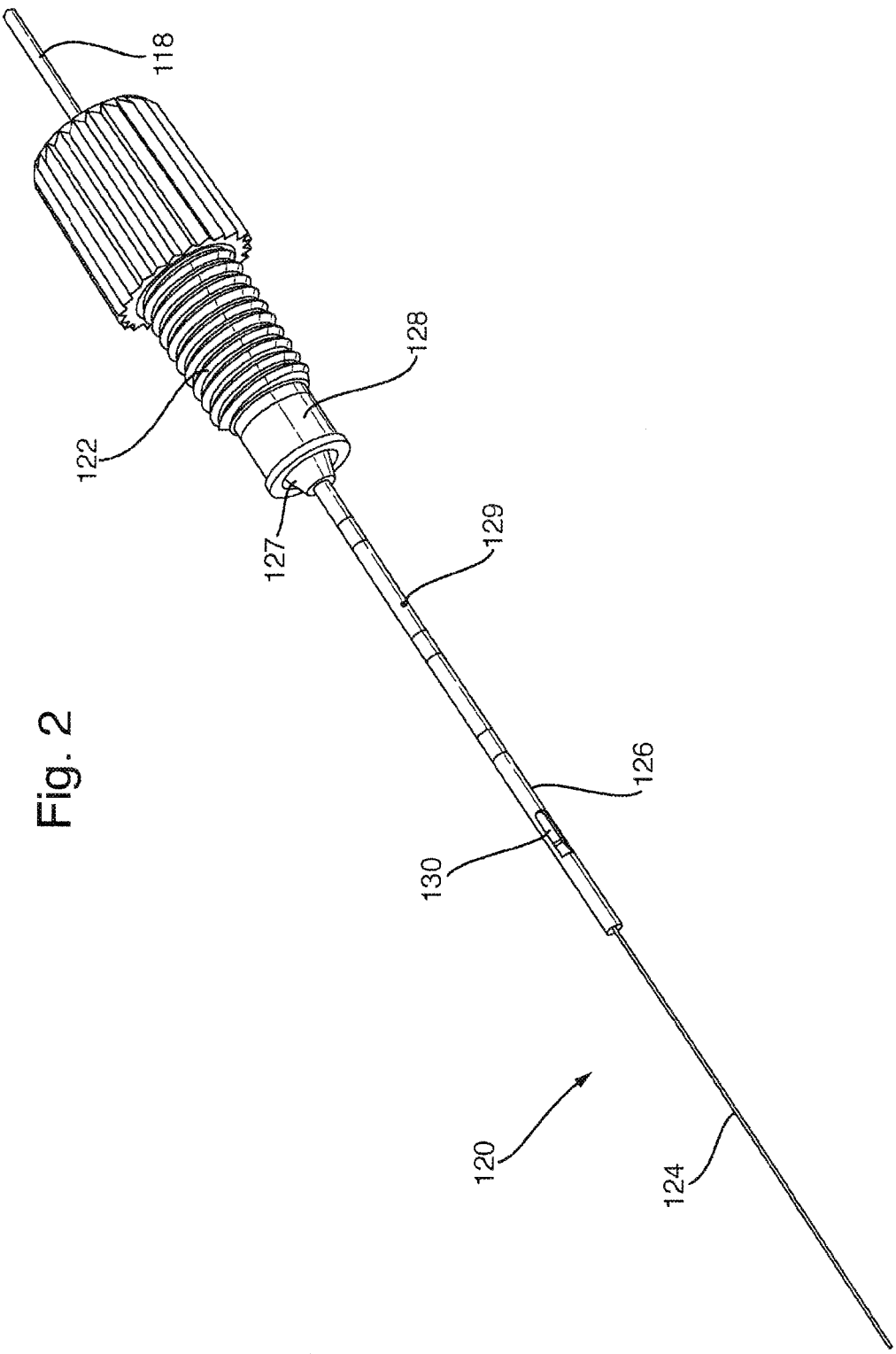
FIG. 2 is an illustration of the outlet end of the probe assembly of FIG. 1 for being fitted into a mass spectrometer.

FIG. 2 shows the outlet end 120 of the probe assembly in more detail. In use, the outlet end 120 is inserted into the ion source of a mass spectrometer (not shown) and is releasably secured in the mass spectrometer by the outlet attachment fitting 122. The attachment fitting comprises a screw threaded portion on its external surface that engages with and is screwed into a complementary screw thread on the mass spectrometer. The attachment portion 122 may have a ratchet fitting for securing the probe to the mass spectrometer. The insulating fluid line 118 runs from the fluid inlet 116 at the inlet end 112 to an electrically conductive capillary 124 that forms a fluid outlet at the outlet end 120. The electrically conductive capillary 124 may be formed, for example, from steel. The electrically conductive capillary 124 makes a joint (not shown) with the electrically insulating fluid line 118 at a location downstream of the outlet attachment fitting 122. This is described in relation to FIG. 3. This arrangement ensures that only electrically insulated tubing extends out of the mass spectrometer from the attachment fitting 122, thereby reducing the risk of electrocution of the user. The electrically conductive capillary 124 receives eluent from the insulating fluid line 118 and delivers it into the mass spectrometer, when the outlet end 120 is attached to the mass spectrometer.

It is desired to supply a voltage to the electrically conductive capillary 124 whilst spraying eluent into the mass spectrometer. This voltage is supplied by the mass spectrometer to the outlet attachment fitting 122 and must then be conveyed from the outlet attachment fitting 122 to the electrically conductive capillary 124. However, as mentioned above, the electrically insulating line 118 extends between the attachment fitting 122 and the electrically conductive capillary 124. As such, an electrically conductive member 126, in the form of a tube, is arranged to extend between an electrical connection on the attachment device 122 and the electrically conductive capillary 124 so as to transmit a voltage from the attachment device 122 to the electrically conductive capillary 124. The electrically conductive member 126 covers the part of the electrically insulating fluid line 118 which passes downstream of the outlet attachment fitting 122, the joint (not visible) and part of the electrically conductive capillary 124. The end of the electrically conductive capillary 124 is arranged to extend out from the electrically conductive tube 126. A conductive ferrule 127 may form the electrical connection on the outlet attachment fitting 122 that provides an electrical connection between the housing of the mass spectrometer (not shown) and the electrically conductive tube 126. An electrical connection (e.g. tabs 130) is also arranged between the electrically conductive tube 126 and the electrically conductive capillary 124 to allow the voltage to pass to the electrically conductive capillary 124.

A fluid bleed hole 129 may be provided in the conductive member 126 for allowing fluid to bleed into the mass spectrometer source if the joint between the conductive capillary 124 and the insulating fluid line 118 fails. This prevents fluid bleeding out of the mass spectrometer, which may be a potential source of electrocution or cause hazards to the instrument.

Figure 3:
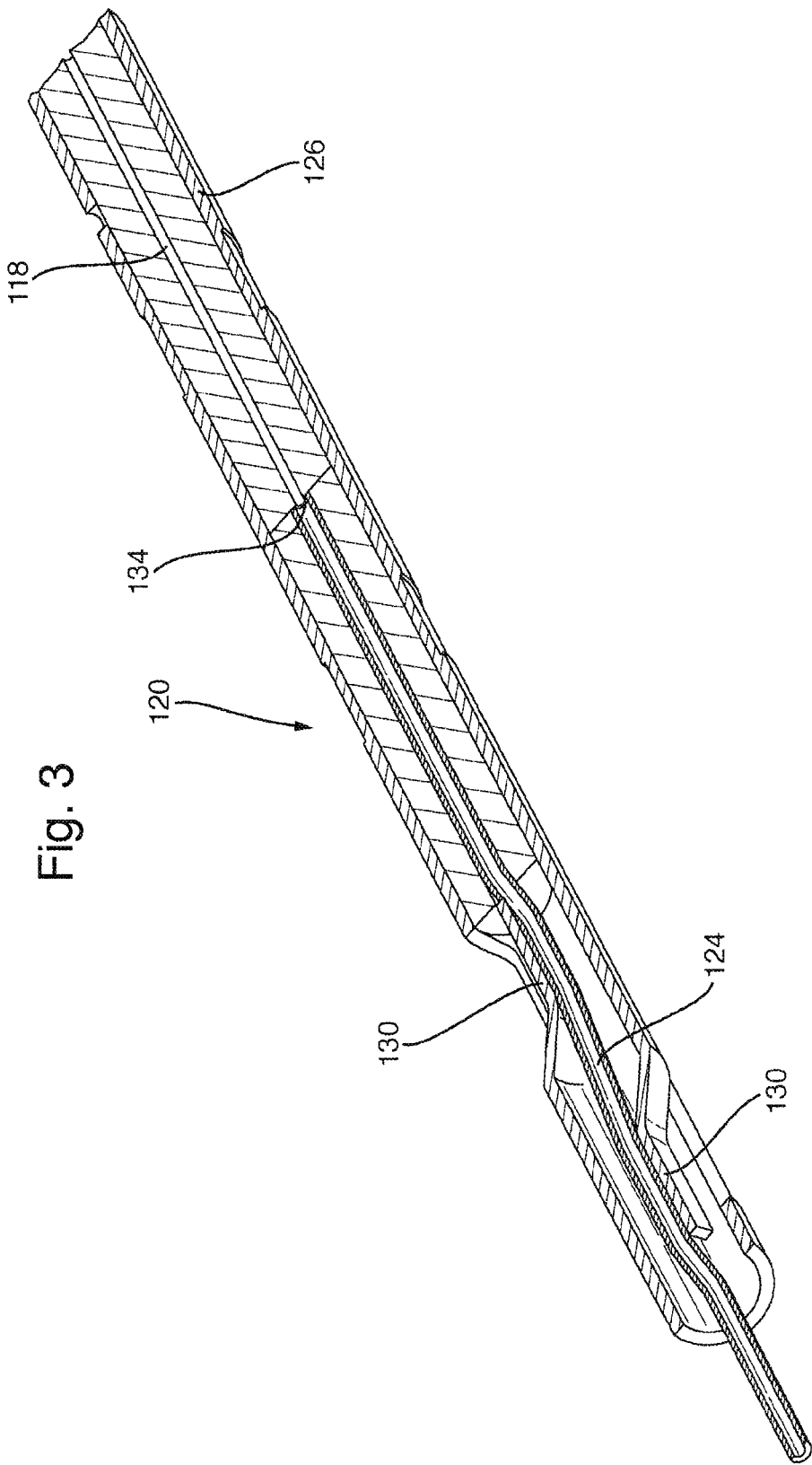
FIG. 3 is a detailed view of the outlet end of the probe showing the conductive capillary and surrounding conductive member.

FIG. 3 is a detailed cross-sectional illustration of a portion of the outlet end 120 of the probe assembly shown in FIGS. 1 and 2. The insulating fluid line 118 is joined to the conductive capillary 124 at joint 134 such that their bores are in fluid communication. The conductive member 126 extends from an electrical connection on the outlet attachment device 122 (not shown), over the joint 134 and into electrical connection with the conductive capillary 124. As such, a voltage can be supplied from the attachment device 122 to the conductive capillary 124 by the conductive member 126, even though the electrically insulating line 118 extends between the attachment device 122 and the conductive capillary 124.

Metal tabs 130 are cut into, or depressed in, the conductive member 126 so that these tabs 130 of the conductive member 126 contact the conductive capillary 124, thereby making an electrical connection between the two components. At least two tabs 130 are preferably provided, wherein one tab 130 is preferably forced into contact with one side of the conductive capillary 124 and another tab 130 is forced into contact with the other side of the conductive capillary 124. The tabs 130 are arranged relatively close together at axially spaced apart locations. This arrangement serves to hold the conductive capillary 124 in a substantially fixed radial position and ensures constant contact between the conductive capillary 124 and the conductive member 126. This is in contrast to conventional arrangements, wherein the conductive capillary 124 is centrally aligned in a bore and the motion of the nebuliser gas around the conductive capillary 124 causes the capillary 124 to move into intermittent contact with the surrounding tube.

Figure 4:
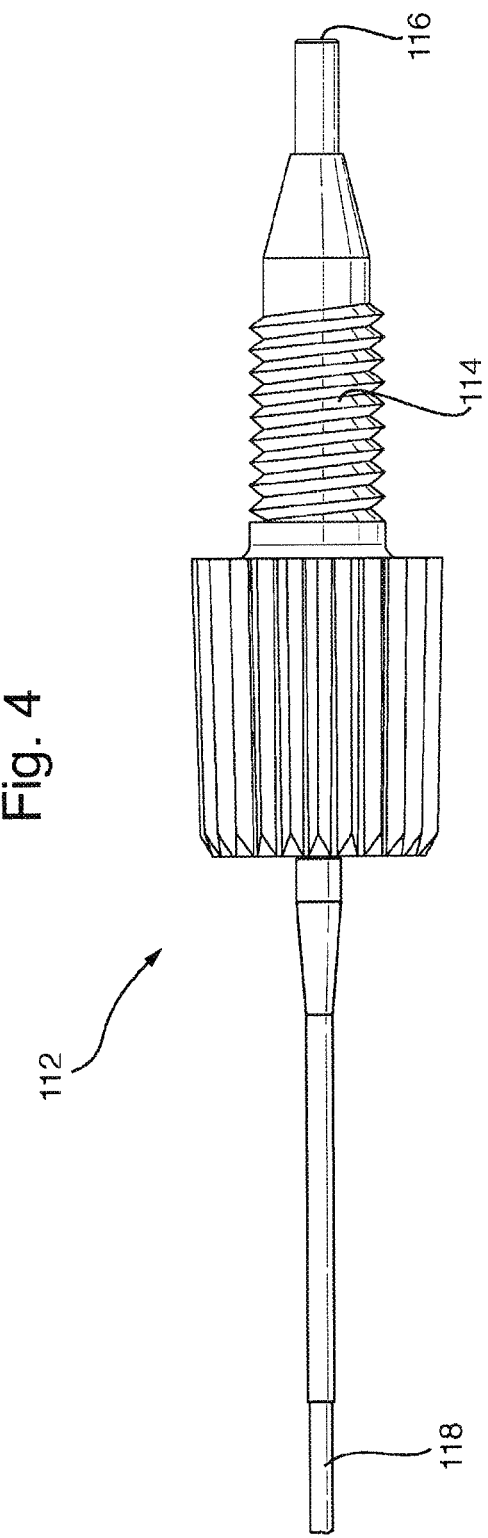
FIG. 4 is an illustration of the inlet end of the probe assembly of FIG. 1 for being fitted into a liquid chromatography device.

FIG. 4 is a detailed view of the inlet end 112 of the probe assembly, i.e. the end to be fitted into the liquid chromatography system. As described in relation to FIG. 1, the inlet end 112 has an inlet attachment fitting 114 for attaching the probe to a liquid chromatography device (not shown). In use, the inlet end 112 of the probe may be inserted into the liquid chromatography device and releasably secured therein. The attachment device may include a screw threaded portion and/or ratchet mechanism for engaging a complementary profile on the liquid chromatography device so as to releasably secure the probe in the liquid chromatography device. A fluid inlet 116 at the inlet end 112 is arranged to receive the eluent from the liquid chromatography instrument. An electrically insulating fluid line 118 runs from the inlet end 116 to the outlet end 120.

Figure 5:
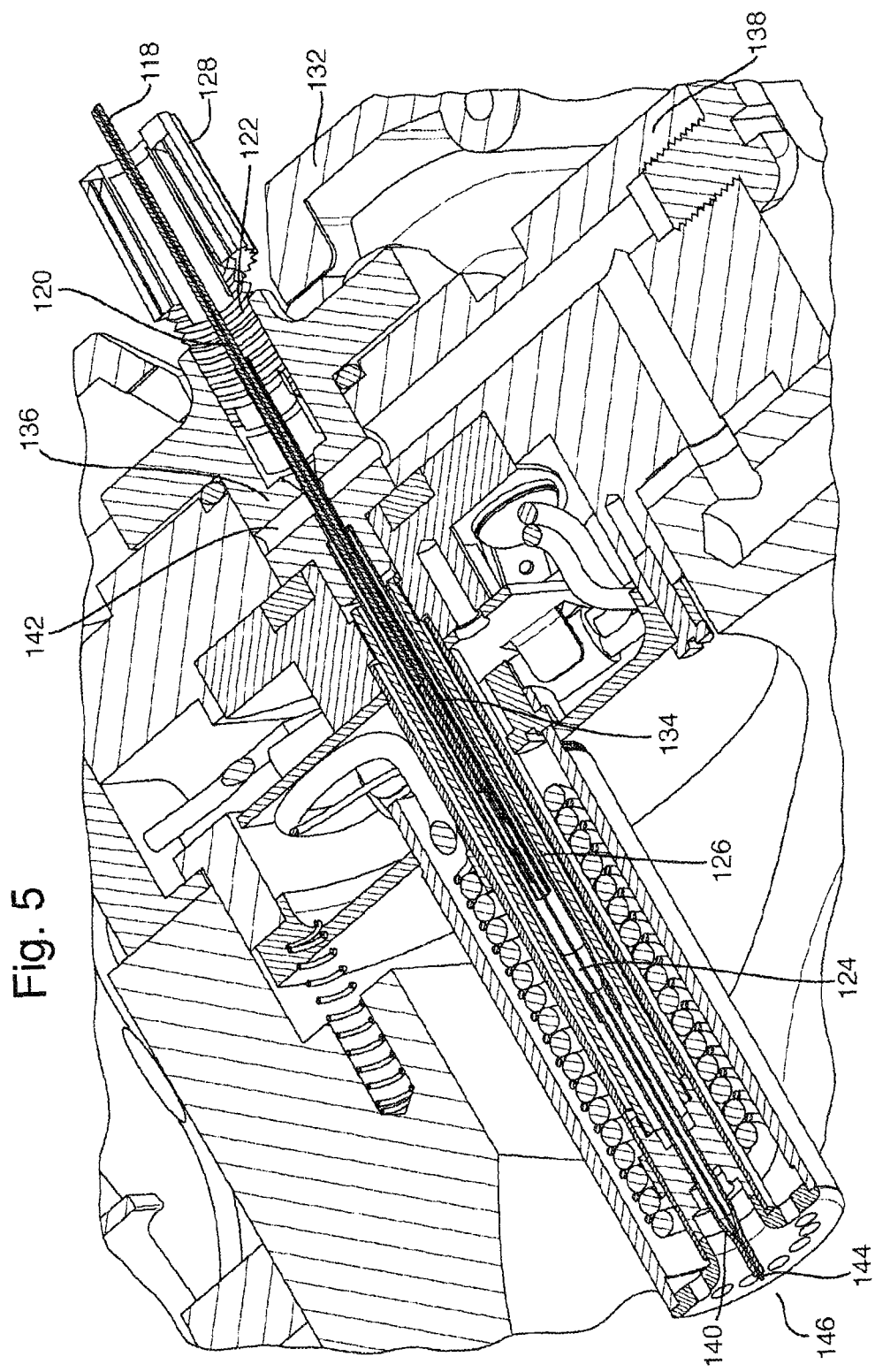
FIG. 5 shows a cross-section through the probe assembly outlet section when inserted into and attached to the mass spectrometer.

FIG. 5 is a cross-sectional illustration of the outlet end 120 of the probe assembly when attached to the mass spectrometer 132. A nebuliser gas tube 140 in the mass spectrometer surrounds the electrically conductive capillary 124, the electrically conductive member 126, the capillary joint 134 between the conductive capillary 124 and the insulating fluid line 118, and part of the electrically insulating fluid line 118. A gas flow is supplied from a nebuliser gas flow entry port 142 along the nebuliser gas tube 140 to the fluid outlet 144. Eluent received from the liquid chromatography device would pass from the fluid inlet 116, through the electrically insulating fluid line 118, the capillary joint 134, through the electrically conductive capillary 124, to the fluid outlet 144, and into the ionisation chamber 146 of the mass spectrometer. The nebuliser gas flow is arranged to flow from the nebuliser gas flow entry port 142, along the nebuliser gas tube 140 towards the fluid outlet 144. The gas flow will flow past the fluid outlet 144 and into the ionisation chamber 146. This enhances or enables the spraying of the eluent from the conductive capillary 124 into the ion source. The voltage on the electrically conductive capillary 124 at the fluid outlet transfers voltage from the electrically conductive capillary 124 to the eluent as it enters the ionisation chamber 146 causing ionisation to occur.

The outlet attachment device 122 preferably comprises a housing and a cup 128, such as a PEEK cup, for providing a sealing face between the attachment device 122 and the mass spectrometer when the attachment device is inserted into the spectrometer. The attachment device 122 also comprises the ferrule 127 that makes an electrical connection between the body of the mass spectrometer (in which the probe is inserted) and the conductive member 126. The ferrule 127 and the peek cup 128 may be crimped to the insulating line 118 such that they do not move or rotate relative to the insulating line 118, capillary 124 or electrically conductive member 126. The attachment device housing may be rotatable about or slidable along the insulating line 118 for use in attaching the attachment device 122 to the mass spectrometer. Preferably, the ferrule 127 and cup 128 do not rotate, but sit in the housing. The attachment device housing may then be rotated so as to screw the attachment device 122 into the spectrometer so that the cup 128 forms a seal with the spectrometer.

When the attachment device 122 is detached, the user is required to pull the probe assembly from the nebuliser tube 140 in order to remove the probe assembly.

Preferably, the attachment device 114 at the inlet end 112 of the probe is able to slide along the fluid line 118 and may be able to rotate about the fluid line 118. This allows the user to push the tube well into the supply fitting of the liquid chromatography device so as to reduce the dead volume. The attachment device 114 may then be rotated so as to screw it into the liquid chromatography device outlet and so as to make a seal therewith. Advantageously, this removes any need to twist the fluid line 118, which would otherwise stress the tube.

The probe is preferably a single assembly that enables a user to connect a liquid chromatography device, or another liquid based separation device, to the ion source of a mass spectrometer in a safe, reliable and easy manner. Preferably the probe is an Electrospray ionisation probe.

The probe may have a range of variants suited to different applications. For example, the probe may be provided with different bore sizes for the fluid outlet diameter, different variations of the length of the capillary, different capillary sizes (diameters) and different lengths of electrically insulating fluid line.

In order to change the capillary in prior art probes requires the probe to be removed from the mass spectrometer and can take a skilled user approximately 30 minutes to change the capillary. The procedure requires tools to be used. Common designs of prior art probes also require a connection from the liquid chromatography device to the fluid inlet of the probe. This connection may be made using conventional labware screw fittings. Leaks of fluid and gas at these points are common. This may present an issue due to the loss of sample or the leaking of undesirable solvents or gas into the laboratory environment.

The present invention is advantageous over the prior art probes, which are typically large and complex assemblies mounted to the mass spectrometer ion source. In prior art probes, when the capillary requires replacing, the capillary must be removed and replaced using mechanical fixtures and tools. In contrast, the present invention is preferably a single assembly which does not require the use of tools to attach the probe to the mass spectrometer.

Electrospray ion sources of the prior art require voltages to be connected to the probe in order to ensure that a high voltage is passed to the fluid capillary. This voltage is required to be supplied to the capillary for the desolvation process of the sample and for charged droplet formation within the ion source. As such these probes require high voltage cables to be attached. This can result in a danger of electrical shock for a user, particularly should there be any fluid leak from the instrument. The preferred embodiment of the present invention is designed to ensure that this danger is removed, by removing the danger of a fluid leak and by ensuring that a high voltage can only be applied when the probe is sealed to the spectrometer housing. One or more sensor may be provided for preventing the voltage from being applied until the probe is tightly screwed into the mounting of the mass spectrometer.

Although the present invention has been described with reference to preferred embodiments, it will be understood by those skilled in the art that various changes in form and detail may be made without departing from the scope of the invention as set forth in the accompanying claims.

The preferred embodiment of the present invention presents a single assembly which is cheap to produce, and may be a disposable unit.

The outlet attachment device may comprise a screw torque fitting for preventing the incorrect fitting of the outlet attachment device by over tightening it.

The ferrule may be made from a metal or an electrically conductive polymeric material.

Preferably, no external electrical cables are required to be attached to the probe.

The high voltage may be applied to the nebuliser tube assembly internally within the ion source and passed from the nebuliser tube assembly to the probe assembly via the ferrule. Alternatively, the high voltage may be passed directly from the ferrule to the electrically conductive tube.

The joint between the conductive capillary and insulating fluid line is located downstream of the outlet attachment device, i.e. within the ion source when the probe is attached to the spectrometer. Due to this arrangement, in the event of any leaks in the probe, the leaks cannot escape outside the mass spectrometer housing.

In the preferred embodiment the outlet attachment device preferably comprises a releasable attachment for releasably attaching the probe to the spectrometer. The attachment device may comprise a screw joint, a clamp, a bayonet, or any other form of attachment means which does not require tools to fit. In less preferred embodiments the attachment device may be a device which requires tools to fit. The inlet attachment device may comprise one of these attachment mechanisms or attaching the probe to the liquid chromatography device.

The electrical connection from the electrically conductive capillary to the electrically conductive member may be using tabs, as depicted in the figures. Alternatively, other methods of electrical connection may be used. For example, other methods of connection may include small bends or bumps in the electrically conductive tube, holes to stitch or weave the electrically conductive tube through or offsets in the electrically conductive tube. The electrical connections may be provided in the probe prior to the capillary being passed through in the manufacturing process. This may create difficulties during manufacture or time to be added during manufacture. Stitching the capillary through the electrically conductive tube and pushing the capillary through the electrically conductive tube may cause the capillary to bend or roll, which may cause problems during in use. Dimples in the tube may best be performed with the capillary in place but this may be more difficult due to the danger of damaging the capillary during this process. It will also be appreciated by the skilled person that working the capillary may pull the capillary, which could put stress on the crimped joint. Thus, in the preferred method of manufacture, the joint is made crimped and tested. The tabs may be pre-cut into the electrically conductive tube at this point but not formed. After the crimping is performed, and the joint tested, the tabs may then be bent down into contact with the capillary. In this process, the tab stops before crushing the capillary.

Preferably the capillary and/or conductive tube member are straight. The tabs of the preferred embodiment do not crush the capillary but form an S-bend to gain the connection with the capillary.

The electrical connection between the electrically conductive capillary and the electrically conductive member may be created by the use of an electrically conductive packing material between the electrically conductive capillary and the electrically conductive member.

The various components of the probe assembly preferably have a fixed geometry relative to each other and are set with tolerances so as to position the capillary tip at the opening of the nebuliser tube with the optimal protrusion position. This is desirable so that the user does not need to make any adjustments or optimising to the positioning after fitting the probe to the spectrometer.

The probe is preferably constructed so as to reduce the presence of dead volume both within the probe assembly and where the connection to the liquid chromatography device is made. This will aid the chromatographic separation and reduce band broadening of the separated eluent.

Probes may be provided in a range of configurations relating to bore sizes and capillary lengths which are suited to specific applications or to make minimal tidy tubing connections between the liquid chromatography and mass spectrometry devices.

The outlet end of the probe is preferably configured to fit into the nebuliser tube of a mass spectrometer. The nebuliser gas flow may enter the nebuliser tube through two ports. The nebuliser gas may flow past the probe assembly and through a small reduced diameter around the capillary tip where droplet formation and/or desolvation occurs.

The probe may be configured for miniature or smaller mass spectrometers.

Preferably, the outlet and/or inlet attachment device (optionally together with the spectrometer) is configured so as to produce an audible click when the attachment device is fitted securely to the spectrometer.

The apparatus may be arranged to alert the user of any potential leaks that may be caused by incorrect attachment of the probe assembly. Incorrect attachment may cause gas or fluid to leak near the ferrule or attachment device. A source pressure test procedure may detect and alert the user to such an issue. If the attachment device is not secured tightly enough to the spectrometer the source pressure test may detect a source leak. This may be detected in software, and result in an error being alerted to the operator when attempting to operate the mass spectrometer. The user may be alerted to the leak by as a loud hissing noise.

The conductive ferrule may form a seal with the electrically conductive member. This may be provided so as to reduce the danger of leaks into the laboratory in which the instrument is placed. A second, further seal may be provided between the cap and the mass spectrometer housing so as to ensure that even in the event of failure of the seal between the conductive ferrule and the electrically conductive tubing no leakage into the laboratory may occur.

If the joint between the electrically conductive capillary and the insulated fluid line fails internally, the user may be alerted to this by a loss or degradation of data produced by the instrument.

Although the preferred embodiment has been described for use in an electrospray ion source, it may be used in other types of ion source such as an atmospheric pressure chemical ionisation source (APCI) or an impactor spray ion source. In these embodiments, the probe assembly would not need to have electrical connections to provide a high voltage to the electrically conductive capillary.

The invention claimed is:

1. A probe assembly comprising:
   an inlet for receiving an eluent from a chromatography device;
   an outlet for delivering the eluent to an ion source of a mass spectrometer; and
   an attachment device for attaching the outlet to the mass spectrometer;

wherein the outlet comprises an electrically conductive capillary and an electrically conductive member surrounding at least part of the electrically conductive capillary;

wherein the probe assembly comprises an insulating fluid line for transporting eluent from the inlet to the electrically conductive capillary and a joint between the insulating fluid line and the electrically conductive capillary, wherein the joint is downstream of the attachment device;

wherein an outer surface of the attachment device comprises a first electrical contact for receiving a voltage from the spectrometer when the attachment device is attached thereto, wherein the first electrical contact is connected to the conductive member and the conductive member is connected to the conductive capillary for transmitting the voltage from the spectrometer to said conductive capillary; and wherein said joint is downstream of the first electrical contact.

2. The probe assembly of claim 1, wherein the outlet of the probe is configured to be insertable into an orifice of the mass spectrometer and the attachment device is configured so as to releasably engage the orifice so as to releasably attach the probe to the mass spectrometer.

3. The probe assembly of claim 1, wherein the attachment device comprises a screw fitting, a clamp, or a bayonet on an external surface of the attachment device.

4. The probe assembly of claim 1, wherein the electrically conductive member is an electrically conductive tube.

5. The probe assembly of claim 1, wherein the electrical connection from the electrically conductive member to the electrically conductive capillary is performed by tabs in the electrically conductive member; and/or wherein the electrical connection from the electrically conductive member to the electrically conductive capillary is performed by an electrically conductive packing between the electrically conductive member and the electrically conductive capillary.

6. The probe assembly of claim 1, wherein the electrically conductive member is arranged to receive said voltage upon connection of the attachment device to the mass spectrometer through an electrically conductive ferrule.

7. The probe assembly of claim 1, wherein the electrically conductive capillary is an electrospray capillary.

8. The probe assembly of claim 1, wherein the inlet for receiving the eluent is spaced from the attachment device.

9. The probe assembly of claim 1, wherein the probe has an inlet attachment device disposed towards one end of the probe and an outlet attachment device disposed towards the other end of the probe; and the inlet attachment device is suitable for attaching an inlet to a chromatography device.

10. A probe assembly for receiving eluent and delivering it through an orifice in a housing of a mass spectrometer or ion mobility spectrometer, said probe assembly comprising:
an electrically insulated fluid line having a fluid inlet for receiving eluent;
an electrically conductive capillary joined to said fluid line for receiving said eluent and having a fluid outlet for delivering the eluent into said spectrometer;
an attachment member surrounding said insulated fluid line, wherein the joint between the insulated fluid line and the conductive capillary is located downstream of the attachment member, and wherein the attachment member is configured to releasably engage the spectrometer when the capillary and part of the fluid line are inserted through said orifice;
a first electrical contact on an outer surface of said attachment member for engaging an electrical contact on said spectrometer when the capillary and fluid line are inserted through said orifice and the attachment member is releasably engaged with the spectrometer; and
a conductive member extending downstream from said electrical contact, beyond said joint between the insulated fluid line and the capillary, and into contact with said capillary for supplying a voltage from said first electrical contact to said capillary, wherein said joint is downstream of the first electrical contact.

11. The probe assembly of claim 10, wherein the attachment member comprises a screw fitting, a clamp, or a bayonet on an external surface of the attachment device for releasably engaging the spectrometer when the capillary and fluid line are inserted through said orifice.

12. The probe assembly of claim 10, wherein the electrically conductive member is an electrically conductive tube that extends from the first electrical contact on the attachment member to the capillary.

13. The probe assembly of claim 10, wherein the electrically conductive capillary is an electrospray capillary.

14. The probe assembly of claim 10, wherein said attachment member is disposed towards an outlet end of the probe assembly and the probe assembly has another attachment member disposed towards inlet end of the probe assembly for attaching the inlet to a chromatography device or other source of analyte solution.

15. A system comprising a mass spectrometer or ion mobility spectrometer and the probe assembly of claim 10, wherein the spectrometer comprises a housing having an orifice therein for receiving said probe assembly therethrough, wherein the attachment member of the probe and the spectrometer housing are configured such that the attachment member is releasably engagable with the orifice so as to connect the probe assembly to the spectrometer with the capillary and part of the insulated fluid line inserted through the orifice, wherein the spectrometer comprises a voltage supply and a second electrical contact, and wherein the second electrical contact is arranged in the spectrometer so as to engage the first electrical contact on the probe assembly when the probe assembly has been releasably engaged with the orifice.

16. A method of delivering eluent to a mass spectrometer or ion mobility spectrometer comprising:
providing a system as claimed in claim 15;
inserting the outlet end of the probe assembly into said orifice;
releasably engaging the attachment member of the probe assembly with the spectrometer such that the first electrical contact of the probe assembly engages the second electrical contact of the mass spectrometer;
supplying said voltage to said second electrical contact such that the voltage is applied to the conductive capillary; and
supplying eluent into the insulated fluid line such that the eluent is transmitted through the conductive capillary and into the spectrometer.

* * * * *